United States Patent [19]

Leung et al.

[11] Patent Number: 4,733,653

[45] Date of Patent: Mar. 29, 1988

[54] RADIOTHERAPY APPARATUS

[75] Inventors: Philip K. M. Leung, Agincourt; Henry P. J. Webb, Toronto, both of Canada

[73] Assignee: The Ontario Cancer Institute, Toronto, Canada

[21] Appl. No.: 802,200

[22] Filed: Nov. 25, 1985

[51] Int. Cl.[4] ...................... A61M 37/04; A61N 5/10; G21F 5/02

[52] U.S. Cl. ................................. 128/1.2; 250/494.1; 250/497.1

[58] Field of Search ................................ 128/1.1, 1.2; 250/497.1, 494.1

[56] References Cited

U.S. PATENT DOCUMENTS

| 2,750,517 | 6/1956 | Baum | 128/1.2 |
| 3,351,049 | 11/1967 | Lawrence | 128/1.2 |
| 3,515,876 | 6/1970 | Smith et al. | 250/106 |
| 4,190,461 | 2/1980 | Hedger | 128/1.2 |
| 4,233,517 | 11/1980 | Van't Hooft | 250/497 |

FOREIGN PATENT DOCUMENTS

| 479311 | 11/1969 | Switzerland | 128/1.2 |
| 279814 | 11/1975 | U.S.S.R. | 128/1.1 |

Primary Examiner—Kyle L. Howell
Assistant Examiner—John C. Hanley
Attorney, Agent, or Firm—Ridout & Maybee

[57] ABSTRACT

In radiotherapy use is made of apparatus of the type in which a chain of balls comprising radioactive balls and inert spacer balls is moved pneumatically to and from an applicator tube within the patient, the spacer balls are made of a material such as nylon which is softer and less dense than the radioactive balls, and is radiographically transparent. This reduces wear and tear on the radioactive balls and facilitates control of dosage and monitoring of the treatment. The balls are sorted after use by means of a radiation detector. The ball chain has a large diameter end ball of ferromagnetic material, which blocks air flow through the applicator when correctly located therein, and whose position can be verified by an induction coil. By assembling and storing the chain in a storage tube having two air inlets, respectively above and below the end ball, and choking the lower inlet, air may be selectively applied to the inlets to expel the chain from the storage tube either with its end ball for transport to the applicator tube, or without its end ball for sorting. Use of the lower inlet alone enables pressure retaining the chain in the applicator to be maintained only in the absence of air flow through the applicator tube, thus enabling malfunctions to be detected.

15 Claims, 3 Drawing Figures

RADIOTHERAPY APPARATUS

BACKGROUND OF THE INVENTION

1. Field of the Invention

This invention relates to apparatus for applying intracavitary radiotherapy.

2. Description of Related Art

Apparatus for this purpose is disclosed in U.S. Pat. No 4,233,517 issued Nov. 11, 1980 to Van't Hooft, which in turn refers to a French Pat. No. 1,593,557. In the type of apparatus described in these patents, radioactive material is conveyed to a desired location within the patient by transporting a chain of balls pneumatically to and from an appropriately inserted applicator, the ball being made up of radioactive balls appropriately spaced by non-radioactive metallic balls. The ball chain is assembled and stored prior to use and sorted after use in a control unit within which the balls are transported pneumatically and sorting is carried out magnetically. This entails that the spacer balls are of magnetic material, in practice steel. The radioactive balls consist of a radioactive filling within a comparatively thin stainless steel shell, and the spacer balls usually substantially outnumber the radioactive balls.

The balls are subjected to a great deal of manipulation both in the control unit and in transit to and from the patient, for example, the ball chain must be returned to the control unit every time a nurse or visitor wishes to enter the room in which the patient is being treated, and every time it is desired to alter the configuration of the ball chain. The massive nature of the spacer balls results in considerable battering of the radioactive balls during such manipulation, with the attendant risk of rupture or leakage, and this severely limits the amount of manipulation which can be tolerated since a ruptured or leaky ball is likely to distribute radioactive material throughout the system entailing a time-consuming, hazardous and very expensive clean-up and rebuilding operation. This problem restricts the possibilities for changing the ball chain configuration during the course of a treatment, and also severely restricts access to the patient by other personnel. Even with appropriate precautions, the risk of ball leakage or rupture still exists. A further disadvantage of the steel spacer balls is that they provide partial shielding of the radioactive balls, requiring compensation when calculating radiation dosage, and that they are radiographically opaque which limits the information which can be obtained from check-film radiography.

SUMMARY OF THE INVENTION

An object of the present invention is to provide a system in which the wear and tear on the radioactive balls can be greatly reduced, and which can allow greater flexibility in operation.

According to the invention, a ball chain for use in radiotherapy treatment comprises a plurality of radioactive balls separated by non-radioactive spacer balls of radiographically transparent material of lower density and surface hardness than the radioactive balls.

The invention also extends to radiotherapy treatment apparatus comprising a storage, sorting and assembly system for radioactive balls and non-radioactive spacer balls of radiographically transparent material of lower density and surface hardness than the radioactive balls, the system including a sorter comprising a radiation detector, means to transport the balls past the radiation detector, and means receiving the radiation detector output and operative to divert the balls into different ball storage compartments depending upon whether or not the radioactive detector output exceeds a predetermined threshold, an assembler comprising means for selectively and successively releasing balls from said ball storage compartments into a ball chain store to assemble a ball chain, means for pneumatically conveying a ball chain between the ball chain store and a remote applicator tube for location within the body of a patient, and means for pneumatically conveying a ball chain from the ball chain store to the sorter.

Preferably the ball chain includes an end ball of larger diameter and having a physical property detectably different from that of the remaining balls. Typically this ball may be of ferromagnetic material, and it is restricted to movement along a path between the ball row store and the applicator. By use of techniques for detecting such material, correct location of the ball chain can readily be verified. Damage to radioactive balls by the ferromagnetic ball can readily be avoided since spacer balls will be interposed between the end ball and any of the radioactive balls.

A further feature of the invention provides improved means for transporting the ball chain between the ball chain store and the applicator tube and verifying location of the chain. In the prior art, the pneumatic pressure utilized to transport the ball chain to the applicator tube is maintained during treatment, and the pressure in a tube through which the chain is transported is sensed to determine whether it is sufficient to maintain the chain in the applicator tube. This arrangement does not necessarily provide positive verification of proper positioning of the chain, since it is possible for balls to lodge short of their proper positions without always causing the pressure sensed to drop to a level that will indicate a malfunction. In order to overcome this problem, the applicator tube may include means to sense the presence of the end ball into a predetermined location, for example by sensing the inductance of a coil wound around the tube at that location, and the pneumatic transportation means includes means for supplying air to the tube through two alternative ducts, one of which includes a choke, and a valve seat engageable by said end ball at the predetermined location within the applicator tube, such that the air supplied through the choked duct is insufficient to maintain pressure within the system unless the end ball is seated on the valve seat. The end ball may be retained in the chain store when returning the remaining balls to the sorter by arranging that the choked duct enters the ball store upstream of the normal position therein of the end ball, and that the other duct enters the chain store downstream of the end ball but upstream of the remaining balls. Said other duct is used only during transportation of the ball chain, whilst the choked duct is used whenever the balls are to be moved to or maintained in the applicator duct.

Further features of the invention will become apparent from the following description of a preferred embodiment with reference to the accompanying diagrammatic drawings.

SHORT DESCRIPTIONS OF THE DRAWINGS

Figure 1:
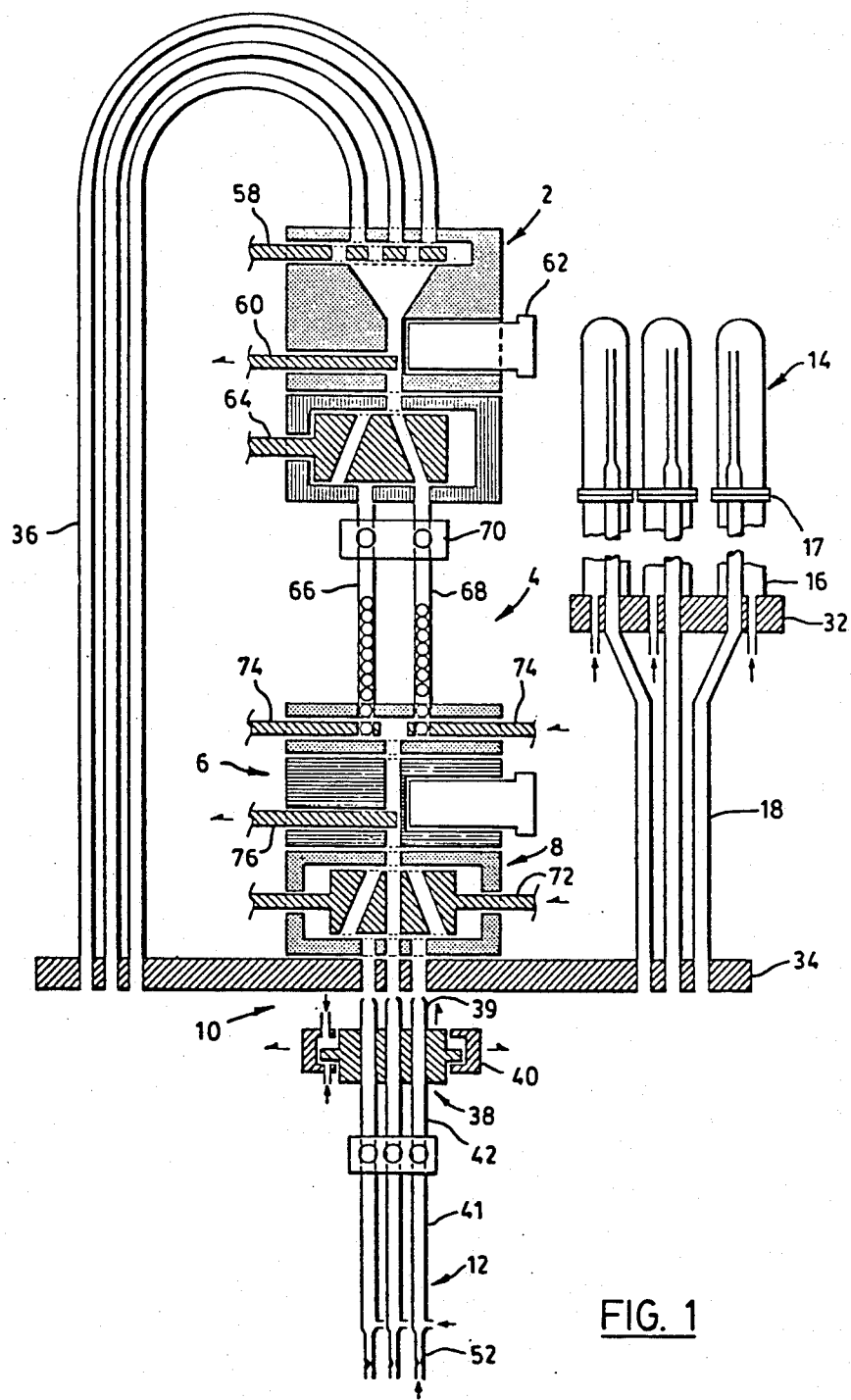
FIG. 1 is a diagrammatic sectional view of radiotherapy treatment apparatus embodying the invention.

Referring to FIG. 1, the apparatus broadly comprises a sorter 2, a ball store 4, a ball selector 6, a channel selector 8, a function selector 10, ball chain stores 12 and applicator tubes 14.

DESCRIPTION OF THE PREFERRED EMBODIMENT

Figure 2:
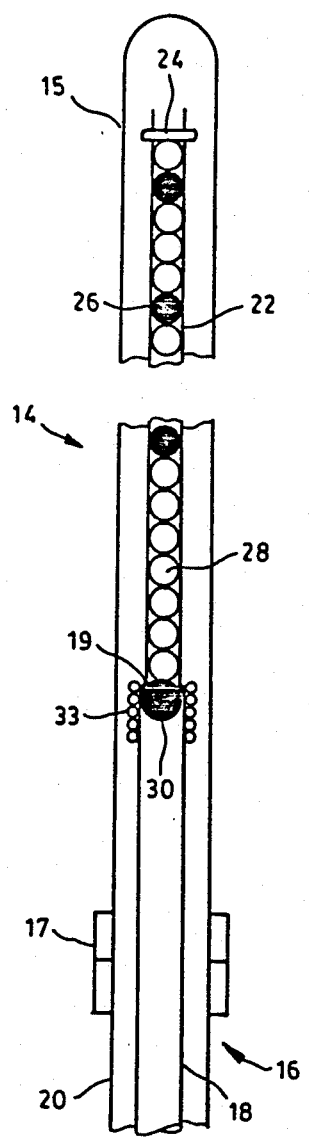
FIG. 2 is a diagrammatic sectional detail showing an applicator tube incorporated in the apparatus, showing a ball chain therein.

An applicator tube 14 is shown in more detail in FIG. 2. This tube has a blind ended outer tube 15 intended for insertion in a body cavity of a patient and is connected by a suitable quick-connect coupling 17 to a carrier tube 16 which comprises two concentric flexible nylon tubes 18 and 20 which connect the applicator tube to the remainder of the apparatus, which can be located in a different room from the appropriately shielded treatment room containing the patient. The inner tube 18 is connected within the applicator tube to a source chain tube 22 of somewhat smaller diameter, the far end of which is bridged by a nylon stopping pin 24 which prevents the passage of a chain of radioactive balls 26 and spacer balls 28, but permits the passage of air. Typically the balls 26 and 28 are 25 mm in diameter, whilst the tube 22 is 2.65 mm in internal diameter, which allows movement of the balls in a chain into the tube except for an end ball 30 of 3 mm diameter. The internal diameter of the tube 18 is typically 3.2 mm, permitting passage of all of the balls.

To initiate treatment, pneumatic pressure is applied to the tube 18 to move a chain of balls 26, 28 and 30 into the applicator tube 14 so that the balls 26 and 28 fill the tube 22 and the ball 30 seats against a shoulder 19 between the tubes 18 and 22, this both holding the balls 26 and 28 in position and cutting off air flow through the tubes 18 and 22. The ball 30 is of ferromagnetic material, typically steel, so that its location may be verified by measuring the inductance of a coil 33 wound around the end of the tube 18. Connecting leads to the coil may pass along the space between the tubes 18 and 20.

Typically, there will be 48 balls 26 and 28 in the chain, the arrangement of the two types of ball depending upon the required pattern and magnitude of the radiation dosage to be administered to a patient. Usually each radioactive ball 26 will be flanked on each side by one or more inert spacer balls. The radioactive balls are of known construction, comprising a relatively thin stainless steel shell with a filling containing an appropriate radiation source. Typical balls are 2.5 mm diameter spherical Cs-137 sources such as type CDC from Amersham Corporation.

The balls 28 should be non-radioactive, should be of material that remains stable under the influence of radioactivity, should be of low density, should be softer than the balls 26, should retain their shape and be wear resistant and should be substantially radiographically transparent. Whilst a number of synthetic plastics materials have the potential to meet these requirements, suitable balls made from nylon are commercially available, and this material meets all of the above criteria as well as having an advantageous self-lubricating property. The low density of the balls 28 minimizes impact on the balls 26 during transit or when the ball chain is arrested, for example by the pin 24, whilst their relative softness minimizes wear on the balls 26. Their transparency to radiation avoids any masking of the radiation from the balls 26 and also means that they do not show up in radiographic images of the treatment area, thus simplifying interpretation. The lightness of the balls 28 substantially reduces the total weight of the chain, thus providing greater assurance of effective transport of the chain at a given air pressure.

In order to return the chain to the remainder of the apparatus, air pressure is applied to the tube 20, which is normally connected to the atmosphere via a suitable filtering system (not shown) to trap and detect any radioactive particles, and the tube 18 is vented via the filtering system. This expels the balls from the tube 22 and back down the inner tube 18 of the carrier tube 16.

A typical apparatus will have provision for loading several applicator tubes 14. Their carrier tubes 16 end at a coupling 32 at which air is exhausted from or admitted to the tubes 20, whilst the tubes 18 continue to a group of orifices in a valve plate 34 of the function selector 10. Groups of orifices also connect the valve plate to the channel selector 8, and to tubes 36 extending to the sorter 2. The function selector 10 also includes a valve member 38 having a group of spigots 39 movable into alignment with any of the groups of orifices in the plate 34, and means 40 to lift the spigots into coupling engagement with the orifices. The spigots are connected by tubes 42 to the ball chain stores 12.

Figure 3:
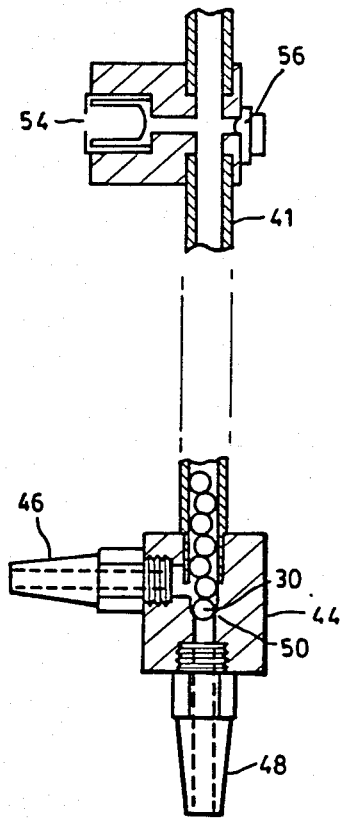
FIG. 3 is a diagrammatic sectional detail showing a ball chain storage tube incorporated in the apparatus.

Referring now also to FIG. 3, in which details of a chain store 12 are shown on a larger scale, each chain store comprises a storage tube 41, typically of 3.2 mm diameter, terminating at its lower end in a top connection of a T-connector 44, the side and bottom connections 46, 48 of which are selectively connected by valves (not shown) to a source of compressed air, typically at 1 atmosphere, or to exhaust via the filter already mentioned. The bottom connection 48 has a valve seat 50 in which the ball 30 is receivable, when the ball chain is in the store, so that air from the side connection 46 is applied between the ball 30 and the remaining balls in the chain. In order to transfer the chain from the store 12 to the associated applicator tube 14, the valve member 38 is moved and lifted to couple the tubes 42 to the tubes 18 and air pressure is applied first to the connection 48 and then the connection 46. Pressure is applied to the connection 48 through a flow restrictor 52. The air applied through the connection 48 will lift the ball 30 out of the valve seat 50, whereafter the air applied through the connection 46 will convey the entire chain through the tubes 42 and 18 to the applicator tube 14. Once arrival of the ball 30 has been detected by the coil 33, the valve controlling the connection 46 is closed. If there is any leakage of air through the system resulting from improper positioning of the chain, then the resulting pressure drop will be detectable because of the choke provided by the restrictor 52.

During return of the chain to the chain store 12, the connections 46 and 48 are vented through the filter. The choking of the connection 48 may provide some cushioning of the chain as the ball 30 enters the seat 50. An infrared source 54 and detector 56 disposed on opposite sides of the tube detect the passage of successive balls, generating pulses which enable the balls to be counted so as to verify the return of the entire chain. The source and detector are so disposed that when the entire chain is present the topmost ball will block passage of light from the emitter to the detector, thus providing further and continuing verification that a complete chain is present in the chain store.

In order to return ball chains from a chain store 12 to the sorter 2, the valve member 38 of the function selector 10 is aligned and raised so that the tubes 42 are connected to the tubes 36, and air pressure is applied to the connections 46 of the appropriate chain store 50 so as to convey the balls 26 and 28, but not the ball 30, to the sorter. The applied pressure will hold the ball 30 on the seat 50 so that it remains in the store 12. An apertured slide 58 in the sorter 2 allows balls to drop one by one onto a shutter 60 which supports them in front of a radiation detector 62. According to whether the output of the detector is above or below a predetermined threshold, a diverter member 64 is moved so that when the shutter 60 is then opened, the supported ball falls into a radioactive ball store formed by a tube 66 or a spacer ball store formed by a tube 68. Movement of the ball into the appropriate tube is verified by photoelectric detectors 70. By comparing the output of detector 62 with additional thresholds and providing additional tubes 66, it is possible to sort radioactive balls of different activity, thus improving the flexibility of the system in providing desired radiation dosages.

In order to assemble a ball chain in a ball chain store 12, the valve member 38 of the function selector is aligned and raised so that the tubes 42 are connected to the orifices in the plate 34 communicating with the channel selector 8. A diverter member 72 in the channel selector 8 is aligned so that balls entering the channel selector are directed into the appropriate tube 42 and hence the selected chain store 12. Balls are admitted to the channel selector 8 from the ball selector 6, which comprises apertured slides 74 which can be selectively actuated to release balls one at a time from any one of the ball stores 66, 68 onto a shutter 76 which holds the balls temporarily whilst a radiation detector verifies whether or not they are radioactive, thus providing a double check on the sorting procedure. Assuming satisfactory verification, the balls are then released by the shutter in the channel selector.

Preferably the mechanical movements, various slides and shutters and the function selector are operated pneumatically by electrically operated valves and the various valves controlling transport of the balls are also operated electrically. These valves are sequenced in a preferred arrangement by electrical control signals generated by a computer under program control, the computer also monitoring the operation of the system and being programmed to initiate appropriate shut-down and alarm signals in the event of malfunction. In FIG. 1, the mechanical parts are shown in a rest condition, and points at which mechanical motion may be selectively applied are shown by half arrows. Points at which pneumatic pressure may be selectively applied are shown by full arrows.

It is found that the use of low density spacer balls of relatively soft material enormously reduces wear and tear on the radioactive balls, which means that restrictions on manipulation of the balls are largely eliminated. This in turn means that restrictions on access to the patient are largely eliminated since the ball chain may be withdrawn without risk of excess wear and tear whenever someone wishes to enter the treatment room, and this withdrawal may be achieved automatically under control of a treatment room door interlock. Moreover, the ball chain may be withdrawn and reassembled at intervals during treatment so as to provide more uniform or more precisely tailored therapy without significantly increasing the risk of damage to the balls.

We claim:

1. In a system for intracavitary radiography comprising a chain of radioactive balls separated by non-radioactive spacer balls, an applicator tube, means to transport the balls pneumatically through a tube to and from the applicator tube, and means to sort the balls from the chain into radioactive and spacer balls, the improvement wherein the ball chain comprises a plurality of radioactive balls separated by non-radioactive spacer balls of radiographically transparent material of lower density and surface hardness than the radioactive balls, whereby battering of the radioactive balls by the spacer balls is avoided, and the spacer balls are distinguished from the radioactive balls by lack of radioactivity.

2. A system according to claim 1, wherein the spacer balls are of nylon.

3. A system according to claim 1, wherein the radioactive and spacer balls are of the same diameter, and the chain includes an end ball of larger diameter and having a further physical characteristic distinguishing it from the remaining balls in the chain, whereby the end ball can be arrested and detected at a shoulder formed at an entrance to the applicator tube.

4. A ball chain according to claim 3, wherein the end ball is of ferromagnetic material.

5. Radiotherapy treatment apparatus comprising a storage, sorting and assembly system containing radioactive balls and non-radioactive spacer balls of radiographically transparent material of lower density and surface hardness than the radioactive balls, the system including a sorter comprising a radiation detector, means to transport the balls past the radiation detector, and means receiving the radiation detector output and operative to divert the balls into different ball storage compartments depending upon whether or not the radioactive detector output exceeds a predetermined threshold, an assembler comprising means for selectively and successively releasing balls from said ball storage compartments into a ball chain store to assemble a ball chain of predetermined length, means for pneumatically conveying a ball chain between the ball chain store and a remote applicator tube for location within the body of a patient, and means for pneumatically conveying a ball chain from the ball chain store to the sorter.

6. Apparatus according to claim 5, wherein the spacer balls are of nylon.

7. Apparatus according to claim 5, wherein the radioactive and spacer balls are of the same diameter, and the chain includes an end ball of larger diameter and having a further physical characteristic distinguishing it from the remaining balls in the chain.

8. Apparatus according to claim 7, wherein the end ball is of ferromagnetic material.

9. Apparatus according to claim 7, wherein the ball chain store comprises a vertical tube of length and diameter sufficient to accommodate a ball chain, a seating at the bottom of the tube to receive the larger diameter end ball of a chain, a first air inlet into the tube immediately above said seating, and a second choked air inlet into the tube immediately below said seating, whereby air may be admitted only to said first air inlet to expel the radioactive and spacer balls from the tube whilst leaving the end ball, to said both inlets to expel the entire chain, and to the second inlet only to permit a limited air flow into the tube.

10. Apparatus according to claim 9, wherein the applicator tube comprises a first tube of a length and diameter just sufficient to accomodate the radioactive and spacer balls but not the end ball, a second tube having one end connected by a shoulder to one end of the first tube and having an opposite end connected to a tube comprised by said means for pneumatically conveying the chain between the ball chain store and the applicator tube, the second tube being of large enough diameter to accommodate the end ball, whereby the latter can seat on said shoulder, and a third tube closed at one end and surrounding the first and second tubes, the other end of the first tube having means to arrest said balls whilst permitting air to pass to or from the third tube to complete a pneumatic circuit through said third tube.

11. Apparatus according to claim 10, wherein the end ball is of ferromagnetic material, and the applicator tube includes an inductance coil wound around the second tube adjacent said shoulder such that its inductance with change detectably according to the presence or absence of the end ball.

12. Apparatus according to claim 9, comprising photoelectric means located at the top of the tube of the ball chain store so as to detect the passage of each ball entering the store, and to detect when the store is full.

13. Apparatus according to claim 5, wherein the means receiving the radiation detector output has plural thresholds, and radioactive balls are divertable into different ball storage compartments dependent upon the threshold exceeded.

14. Apparatus according to claim 5, comprising plural ball chain stores and an applicator tube associated with each ball chain store, and channel selector means operative to direct balls released from the storage compartments into a selected one of the ball chain stores.

15. Apparatus according to claim 14, comprising a function selector means operative to connect the or each ball chain store selectively (a) to said ball storage compartments, (b) to a tube comprising the means for conveying a ball chain to the sorter, or (c) to a tube comprised by the means for conveying a ball chain between the ball chain store and its associated applicator tube.

* * * * *